(12) United States Patent
Hamunen et al.

(10) Patent No.: US 8,680,324 B2
(45) Date of Patent: Mar. 25, 2014

(54) PROCESS FOR SEPARATING STEROLS AND ACIDS FROM TALL OIL PITCH

(75) Inventors: Antti Hamunen, Turku (FI); Juha Orte, Raisio (FI); Reino Kalmari, Espoo (FI); Kosti Mokkila, Tuusula (FI); Marianne Kallio-Meriluoto, Kauniainen (FI)

(73) Assignee: Raisio Nutrition Ltd., Raisio (FI)

( * ) Notice: Subject to any disclaimer, the term of this patent is extended or adjusted under 35 U.S.C. 154(b) by 564 days.

(21) Appl. No.: 12/920,062

(22) PCT Filed: Feb. 27, 2009

(86) PCT No.: PCT/FI2009/050170
§ 371 (c)(1),
(2), (4) Date: Oct. 18, 2010

(87) PCT Pub. No.: WO2009/106696
PCT Pub. Date: Sep. 3, 2009

(65) Prior Publication Data
US 2011/0034725 A1 Feb. 10, 2011

(30) Foreign Application Priority Data
Feb. 29, 2008 (FI) ..................... 20080174

(51) Int. Cl.
*C07C 61/00* (2006.01)
*C07C 61/08* (2006.01)

(52) U.S. Cl.
USPC ........................................ 562/400

(58) Field of Classification Search
None
See application file for complete search history.

(56) References Cited

U.S. PATENT DOCUMENTS

| | | |
|---|---|---|
| 3,887,537 A | 6/1975 | Harada et al. |
| 4,076,700 A | 2/1978 | Harada et al. |
| 4,151,160 A | 4/1979 | Koebner |
| 4,483,791 A | 11/1984 | Phillips, Jr. et al. |
| 6,780,831 B2 | 8/2004 | Hamunen |
| 2002/0107168 A1 | 8/2002 | Hamunen |
| 2005/0033027 A1 | 2/2005 | Rohr et al. |
| 2005/0054866 A1 | 3/2005 | Rohr et al. |

FOREIGN PATENT DOCUMENTS

| | | |
|---|---|---|
| EP | 0952208 A2 | 10/1999 |
| EP | 1081156 A2 | 3/2001 |
| WO | WO-99/16785 A1 | 4/1999 |
| WO | WO-99/42471 A1 | 8/1999 |

*Primary Examiner* — Johann R Richter
*Assistant Examiner* — Jennifer C Sawyer
(74) *Attorney, Agent, or Firm* — Arent Fox LLP

(57) ABSTRACT

The invention relates to a process for recovering sterols and fatty and/or resin acids from tall oil pitch, comprising the steps of:
a) saponifying tall oil pitch to provide saponified tall oil pitch,
b) drying the saponified pitch to obtain dried saponified pitch,
c) subjecting the dried saponified pitch to a first high vacuum evaporation to obtain an unsaponifiable fraction as a distillate and a first residue,
d) optionally subjecting said distillate to a second high vacuum evaporation to obtain an enriched unsaponifiable fraction,
e) crystallizing sterols from the unsaponifiable fraction or the enriched unsaponifiable fraction,
f) acidulating the first residue obtained in step c) to obtain an aqueous phase and an organic phase, separating the aqueous phase and drying the organic phase to obtain a dried organic phase, and
g) subjecting the dried organic phase to vacuum distillation to obtain fatty and/or resin acids and a second residue,
said process additionally comprising providing pitch-based heavy components in the dried saponified pitch in an amount facilitating the first high vacuum evaporation.

17 Claims, No Drawings

PROCESS FOR SEPARATING STEROLS AND ACIDS FROM TALL OIL PITCH

CROSS-REFERENCE TO RELATED APPLICATION

This application is a National Stage entry of International Application No. PCT/FI2009/050170, filed Feb. 27, 2009, which claims priority to Finnish application No. 20080174, filed Feb. 29, 2008, the disclosure of the prior application is hereby incorporated in its entirety by reference.

Tall oil pitch is formed in the following process sequence starting from wood pulping:

Crude sulphate soap (CSS or BLSS) is a by-product of wood pulping and comprises sodium salts of fatty and resin acids and an unsaponifiable neutral fraction which contains sterols and other neutral components, hereinafter called "neutral substances." Crude tall oil (CTO) is made from this soap by acidulation, and tall oil pitch is the distillation residue of CTO when producing tall oil.

The invention especially relates to the separation of the sterol neutral substances by means of high vacuum distillation/evaporation. The invention also relates to the production of fatty and/or resin acids from the residues obtained from the high vacuum distillation/evaporation process.

Some processes for separating unsaponifiable neutral substances from CSS, saponified CTO, or saponified pitch use a high vacuum distillation/evaporation process. These processes take advantage of the volatility differences of volatile unsaponifiables, fatty acid, resin acid, and almost any other non-volatile organic acid soap. In the case of separation by distillation, the difference between the boiling points of volatile products, such as unsaponifiable components, and the boiling point of different organic acid soaps is so remarkable that the separation is very efficient. However, a problem connected with this separation technique is the very high melting point and viscosity of the distillation residue.

U.S. Pat. No. 3,887,537 discloses a process for recovering fatty acids and resin acids from tall oil pitch by saponifying the tall oil pitch with an alkali metal hydroxide (sodium hydroxide) in the presence of an alkyl alcohol (such as butanol) to soaps and unsaponifiables, and then feeding the mixture into a thin film evaporator to evaporate and remove the low-boiling matter including light unsaponifiables, water and alcohol. Subsequently the bottom fraction is fed into a second thin film evaporator for removing unsaponified heavy material including sterols. Finally, the bottom soap fraction from the second evaporator is acidulated with a mineral acid to obtain fatty acids and resin acids. One of the difficulties with this process is that the soaps are very viscous making the handling of these soaps troublesome. The sterol yield is also very low.

U.S. Pat. No. 4,076,700 discloses a process for recovering fatty and/or resin acids from tall oil soap. In this process the unsaponifiables were separated from the soap by distilling in a thin film evaporator at a temperature between the melting point of the soap and 320° C., typically at 310° C. The oily distillate containing β-sitosterol was obtained in a yield of 14.4% on the basis of the tall oil. At such conditions thermal decomposition and/or polymerization of sterols and also acid components is remarkable. Consequently, the process is not in practice optimal.

WO-99/16785 discloses a method for separating unsaponifiable material from tall oil pitch by saponifying the pitch with a mixture of sodium hydroxide and potassium hydroxide to form sodium and potassium salts of fatty acids and resin acids, and then evaporating the unsaponifiable material containing sterols using a thin film evaporator. The unevaporated portion of the pitch which comprises sodium and potassium salts of the saponifiable material is acidulated to generate the resin and fatty acids. Also this method suffers from the difficult material handling of the sodium and/or potassium soaps.

WO-99/42471 discloses a method of separating sterols from tall oil pitch by saponifying the tall oil pitch with an alkali metal base comprising sodium hydroxide, potassium hydroxide or a mixture thereof, followed by neutralizing the saponified pitch with an acid and heating the neutralized pitch to remove water. The thus obtained modified pitch containing free sterols is subjected to evaporation to remove light ends and then the bottom fraction from the evaporation is evaporated using a wiped evaporator to produce a light phase distillate containing free sterols. Subsequently the light phase distillate is dissolved in a solvent comprising an alcohol, and the free sterols are crystallized from the solution by cooling. A disadvantage of this method is that the yield of the sterols is rather low.

U.S. Pat. No. 4,151,160 discloses a process for the separation of fatty acids from the unsaponifiable constituents contained in a head fraction of tall oil by converting the fatty acids into their zinc or lead soaps, and then removing the unsaponifiable constituents by vacuum distillation. Subsequently the non-volatile metal soaps remaining as distillation residue are acidulated to produce the desired fatty acids. Typical components of the light boiling unsaponifiables are long chain alcohols and resin degradation products, and these products have minor commercial value. The content of sterols in the tall oil heads is very low, considerably below 1% by weight, and thus the tall oil head fraction is not suitable as a source for the production of sterols.

U.S. Patent Application 2005/0054866 discloses the isolation of unsaponifiable compounds from tall oil pitch by converting sodium or potassium soaps into metallic soaps which have a lower melting point and have a viscosity sufficiently low to enable distillation processes of the raw material to obtain valuable products including sterols. This process including preparation of metallic soaps is very complicated.

U.S. Pat. No. 4,483,791 discloses a process for the recovery of fatty acids from tall oil heads by converting the fatty acids contained in the tall oil heads into a mixture of magnesium soap and sodium soap, and then vacuum stripping the reaction product. Finally the soaps are acidulated to produce the desired fatty acids.

EP 1 081 156 A2 discloses a process for recovering sterols from mixtures of neutral compounds obtained from e.g. tall oil pitch comprising the steps of distillation, crystallization and recirculation of the mother liquor residue obtained in the crystallization into the first distillation. The residue is rich in sterols and the yield of sterols is thereby improved. No softener is used in this process.

EP 0 952 208 A2 discloses a process for the separation of unsaps from black-liquor soaps or tall oil by dehydrating the raw material, melting and distillation in a short path distillation column. This publication also suggests the addition of unsaponifiables to soap or neutralized tall oil before the drying step in order to reduce the necessary temperature to maintain the mixture at a state of adequate fluidity during the drying process. These added unsaponifiables comprise recirculated unsaps from the process which unsaps are low boiling substances. These recirculated unsaps have a favourable effect on the drying but are believed to have a disadvantageous effect on the subsequent distillation step as the low boiling unsaps are evaporated together with the sterol fraction resulting in a dilution of the sterol fraction.

U.S. Pat. No. 6,780,831 B2 discloses a method, wherein the problems described are solved by adding a high molecular weight softener to the saponified pitch prior to the evaporation of unsaponifiables. Examples of the non evaporated softener are high molecular weight hydrocarbons, e.g. paraffin waxes, high boiling naphthenes, polyglycols, e.g. polypropylene glycol and polyethylene glycol, and high molecular weight silicon oils. These softeners lower the viscosity of the residual saponified pitch and thereby facilitate the evaporation process.

SUMMARY OF THE INVENTION

The present invention relates to a process which avoids the drawbacks of the above described prior art processes, including sterol losses at too high temperatures and incomplete splitting of sterol esters and also the use of external process aids which in turn increases the processing costs and can reduce the reclamation value of the residue fractions as e.g. biofuel.

The present invention is an improvement of the process described in U.S. Pat. No. 6,780,831, providing an economical way to isolate sterol-containing fractions from pitch without any need for external softener chemicals. The principle of the invention is that the high molecular weight components of the pitch (i.e. pitch-based heavy components) or pitch as such can act as the process facilitators instead of the use of an external softener.

DETAILED DESCRIPTION OF THE INVENTION

Thus, the present invention provides a process for recovering sterols and fatty and/or resin acids from tall oil pitch, comprising the steps of:
a) saponifying tall oil pitch to provide saponified tall oil pitch,
b) drying the saponified pitch to obtain dried saponified pitch,
c) subjecting the dried saponified pitch to a first high vacuum evaporation to obtain an unsaponifiable fraction as a distillate and a first residue,
d) optionally subjecting said distillate to a second high vacuum evaporation to obtain an enriched unsaponifiable fraction,
e) crystallizing sterols from the unsaponifiable fraction or the enriched unsaponifiable fraction,
f) acidulating the first residue obtained in step c) to obtain an aqueous phase and an organic phase, separating the aqueous phase and drying the organic phase to obtain a dried organic phase, and
g) subjecting the dried organic phase to vacuum distillation to obtain fatty and/or resin acids and a second residue,
said process additionally comprising providing pitch-based heavy components in the dried saponified pitch in an amount facilitating the first high vacuum evaporation.

Said pitch-based heavy components function as a process aid and/or softener. The role of the softener—like the softener disclosed in U.S. Pat. No. 6,780,831—is to decrease the viscosity of the material in the first high vacuum evaporation, thereby preventing plugging of the equipment and, on the other hand, facilitating the removal of the unsaponifiable fraction from the low viscous liquid material in the evaporation unit. Due to the softener the residue remains liquid at processing conditions.

According to the present invention the required amount of pitch-based heavy components can be provided
i) by recirculating the whole or part (e.g. 5-90%) of the second distillation residue obtained in step g) to the saponified pitch and/or to the dried saponified pitch, wherein the amount of added said residue preferably is between 1% and 50% by weight, more preferably between 2% and 40% by weight, and most preferably between 5% and 30% by weight based on the weight of the dried saponified pitch, or
ii) by adding a heavy fraction separated from pitch to the saponified pitch and/or to the dried saponified pitch, wherein the amount of added said heavy fraction preferably is between 1% and 50% by weight, more preferably between 2% and 40% by weight, and most preferably between 5% and 30% by weight based on the weight of the dried saponified pitch, or
iii) by adding pitch to the saponified pitch and/or to the dried saponified pitch, wherein the amount of added said pitch preferably is between 1% and 50% by weight, more preferably between 2% and 40% by weight, and most preferably between 5% and 30% by weight based on the weight of the dried saponified pitch, or
iv) by choosing a tall oil pitch naturally having a high content of said heavy components, or
v) by adjusting the degree of the saponification of the pitch.

According to the invention it is also possible to use a combination of two or more of the above measures i), ii), iii), iv) and v).

Preferred ways of providing the pitch-based heavy components according to the invention are i), ii), iii), and iv), more preferably i), ii), and iii), still more preferably i) and ii), and most preferably i).

By pitch-based heavy components is meant heavy components, especially heavy hydrocarbons, sterol esters and terpene esters, obtained from tall oil pitch. By pitch-based heavy components are meant pitch-based compounds that are heavier than sitosterol.

For alternatives i) and ii) said second distillation residue and said heavy fraction typically have a composition of which at least 90% by weight, preferably at least 95% by weight, and most preferably at least 99% by weight, are compounds that are heavier than sitosterol.

The amount of pitch-based heavy components facilitating the first high vacuum evaporation has to be determined by testing so as to see when the evaporation is successful. The more severe temperature and vacuum conditions are used in the first evaporation the less heavy components are needed. But sterols are decomposed at too severe conditions. Therefore, if not enough of heavy components are present in the first evaporation more has to be added. Also the quality of the tall oil pitch used in the first high vacuum evaporation is relevant to how much pitch-based heavy components has to be added. E.g. it seems that pitch from pine needs less heavy components than pitch from mixed birch-pine. Typically there should be at least 20% by weight, preferably at least 25% by weight, more preferably at least 30% by weight, still more preferably at least 35% by weight, even more preferably at least 40% by weight, and most preferably at least 45% by weight of pitch-based heavy components in the dried saponified pitch, in the first high vacuum evaporation according to the invention.

Said pitch-based heavy components can comprise pitch as such (P) which can be added to the dried saponified pitch. After the first process cycle the second distillation residue comprising heavy components obtained in step g) is recirculated to the saponified pitch and/or to the dried saponified pitch.

Alternatively, said pitch-based heavy components can be a pitch residue obtained from distillation fractionation of pitch (PP). This can be produced for use in the first process cycle as follows: Pitch is saponified and the formed organic acids in salt form are converted into free acids by acidulation. After the separation of the aqueous phase, the organic phase is dried and all evaporable components are evaporated in a short path evaporator. The distillation residue comprising heavy pitch components is introduced into the first process cycle. After the first process cycle the second distillation residue comprising heavy components obtained in step g) is recirculated to the saponified pitch and/or to the dried saponified pitch.

Suitable pitches from which said pitch-based heavy components are derived include pure pine pitch or pitch obtained from processing of mixtures of soft wood and hard wood, such as pine and birch.

The tall oil pitch can be saponified by using an alkali hydroxide, preferably sodium or potassium hydroxide or a mixture thereof. The alkali hydroxide is preferably used in stoichiometric excess of up to 20%, preferably between 4% and 10%. The saponification temperature is preferably in the range of 150° C. to 220° C., more preferably 170° C. to 200° C., and the saponification time is preferably between 10 and 30 minutes. In the saponification step the esters included in the pitch are hydrolyzed to free alcohols and organic acids in salt form.

The drying in step b) can be carried out in a thin film evaporator or in a short path (wiped film) evaporator. The thin film evaporator is more preferred due to a less expensive equipment. The thin film evaporator preferably operates at a temperature in the range of 100° C. to 250° C., more preferably 180° C. to 220° C., and at a pressure in the range of 500 Pa to atmospheric pressure, more preferably 500 to 20000 Pa.

The first high vacuum evaporation of step c) can be carried out in a short path (wiped film) evaporator. The short path evaporator preferably operates at a temperature in the range of 250° C. to 320° C., more preferably 260° C. to 300° C., most preferably 270° C. to 280° C. and at a pressure of at most 500 Pa, more preferably at most 200 Pa, and most preferably at most 100 Pa.

The second high vacuum evaporation of step d) can be carried out in a thin film evaporator which preferably is equipped with an external condenser and includes a fractionation column. The thin film evaporator preferably operates at a temperature in the range of 170° C. to 290° C., more preferably 230° C. to 270° C. and at a pressure in the range of 10 to 500 Pa, more preferably 20 to 500 Pa.

In the crystallization step e) the sterols can be crystallized by any known method involving a solvent mixture comprising at least one, preferably at least two of the solvents selected from the group consisting of ketones, alkanols, hydrocarbons and water. A preferred solvent mixture comprises methyl ethyl ketone, methanol and water. Another preferred solvent mixture comprises a hydrocarbon, methanol and water.

Other solvents/solvent combinations can be used to crystallize the sterols as well. It is known to one of ordinary skill that for pure pine based raw materials, mixtures of hydrocarbon, methanol and water are suitable. These solvents/solvent combinations include other lower alcohols, their mixtures with themselves and, for example, mixtures with hydrocarbons and/or ketones and/or water.

If necessary the crystallized sterols can be recrystallized.

In step f) the drying of the organic phase is preferably carried out at vacuum.

The vacuum distillation of step g) is preferably carried out at a temperature in the range of 170° C. to 290° C., preferably 180° C. to 200° C. and at a pressure in the range of 50 to 3000 Pa, preferably 100 to 2000 Pa and, more preferably 200 to 1000 Pa. The distillation is preferably done with column systems used in commercial tall oil fractionation plants and using typical temperature and vacuum conditions used at those processes.

Optionally, the process of the invention includes removing trace amounts of interfering impurities such as S (sulphur) and/or PAH (polyaromatic hydro-carbons) by activated carbon or catalytic treatment at suitable point(s) of the process.

The high molecular weight components included in the pitch chemically mostly consist of heavy hydrocarbon fractions and can be isolated from pitch or from treated pitch especially by evaporating the lighter material away especially by using short path evaporation. In this context the term "treated" means hydrolysis or saponification followed by acidulation of the formed saponified acids.

Pitch as such—without saponification or hydrolysis—contain in addition to these high molecular weight compounds and lighter material (fatty acids, resin acids, sterols and terpenes, wax alcohols) also sterol esters which also are considerably heavier components compared to sterols. Hence, pitch with its heavy hydrocarbon type material and sterol esters and/or terpene esters can act as "softener" as well.

The amount of pitch-based softener needed for successful evaporation of the unsaponifiables depends on the quality of the pitch and the way of pretreatment of the pitch. In extreme cases, where the amount of the heavy hydrocarbon fraction in the pitch is high and/or the saponification of the pitch is not complete, the recirculation of the heavy residue to the beginning of the process may be almost unnecessary.

In the following the invention will be described in more detail by means of examples. In this specification % refers to % by weight unless otherwise specified.

EXAMPLES

The materials and the amounts thereof and the conditions of the various steps used in following examples as well as the results obtained are compiled in Table 1.

Example 1

1.1 Saponification 1.325 kg 50% NaOH-solution (5% stoichiometric excess) was added to 10 kg of mixed pine/birch pitch (acid value 25.9; saponification value 88.5 mg KOH/g). The mixture was heated with mixing up to 200° C. for 10 minutes in a closed pressure vessel.

1.2 Manufacture of PP

To the above obtained saponified pitch was added with good mixing sulphuric acid solution (0.87 kg concentrated sulphuric acid in 2 kg water). The temperature was kept at 110° C. in the closed vessel for 15 minutes in order to let the organic and water layers get separated. The water (bottom) layer was drained out.

The organic layer was dried by vacuum at a pressure of about 10000 Pa at 110° C. temperature for 0.5 hours time.

The dried organic phase was evaporated using an UIC KD10 short path evaporator. The evaporation temperature was 280° C. and pressure 100 Pa. The feed rate was about 10 kg/h. The split between distillate and residue was 70/30.

The residue was used as softener (PP) in the following recovery process.

1.3 Recovery of Sterols and Acids from Saponified Pitch

Saponified pitch was prepared as described above at point 1.1. The softener (PP) of point 1.2 was added to the saponified pitch. The mixture was then dried using the same evaporation equipment as at point 1.2. Drying conditions in the series of experiments varied between temperature 160-200° C., pressure 500-2000 Pa.

Evaporation of the unsaponifiable fraction was performed at conditions presented in the Table 1. Results, see Table 1. The conditions (temperature and pressure) as well as the amount of pitch-based heavy components in the first evaporation were suitable to enable the evaporation of the unsaponifiable fraction.

The sterols can be isolated from the distillate by prior known crystallization processes. Optionally a second evaporation can be performed before the crystallization to improve the purity of the sterols.

After evaporation of the unsaponifiable fraction, the first residue was taken to another reactor. 10% sulphuric acid was added at 120° C. with agitation until the water phase started to separate. The pH of a sample from the separated water phase was measured. When pH was below 4, sulphuric acid addition was stopped and the formed acidic water phase was separated. The organic phase was dried by using vacuum at the reaction temperature for about 0.5 hours. Organic acids were evaporated using the same equipment as in the earlier steps of the example (not optimal for fractionation). Conditions, see Table 1.

Example 2

This example was carried out in a similar way as Example 1. In this example the softener used was tall oil pitch as such (P). The conditions (temperature and pressure) as well as the amount of pitch-based heavy components in the first evaporation were suitable to enable the evaporation of the unsaponifiable fraction.

Example 3

This example was carried out in a similar way as Example 1. However, in this example no softener was added. This example shows that if the amount of unsaponifiables in the pitch is high enough additional softener is not necessarily needed.

Example 4

This example was carried out in a similar way as Example 1. However, the pitch used in this example was pure pine pitch and no softener was introduced. This comparison example shows that the distillation failed due to the too high melting point of the first distillation residue. No softener was introduced and the amount of internal softener was too small. However, if more severe temperature and vacuum conditions had been applied this evaporation would most probably have been successful.

Example 5

This example was carried out in a similar way as Example 4. However, in this example the same softener that was used as in Example 1, i.e. PP, was introduced. This example shows that the distillation succeeded due to the introduction of the softener.

In should be noted that the acid recovery was not optimized in any of the above examples.

TABLE 1

| | | EXPERIMENT No (Example) | | | | |
|---|---|---|---|---|---|---|
| | | 1 | 2 | 3 | 4 | 5 |
| Pitch quality | | mixed | mixed | mixed | pine | pine |
| sterol-%, from pitch | | 10 | 10 | 10 | 12 | 12 |
| unsaponifiables-%, in pitch | | 45 | 45 | 45 | 30 | 30 |
| sterols in unsaponifiables, % | | 22.3 | 22.3 | 22.3 | 40.0 | 40.0 |
| Softener type | | PP | P | No | No | PP |
| Distillation of unsaponifiable fraction from saponified dried pitch (first distillation) | | | | | | |
| A | saponified pitch, g * | 359.7 | 4361.3 | 259.7 | 432.5 | 397 |
| B | softener, g * | 74.0 | 1169.7 | 0 | 0 | 53 |
| | A + B | 433.7 | 5531.0 | 259.7 | 432.5 | 450.0 |
| C | softener-% | 17 | 23 | 0 | 0 | 13 |
| D | dist. temp. of sterol fraction, ° C. | 260-290 | 290 | 290 | 290 | 290 |
| E | pressure, Pa | 90-100 | 300-400 | 60 | 60 | 60 |
| | yield of sterol fraction, g * | 145.3 | 1969.0 | 130.1 | distillation failed | 122.0 |
| F | sterol fraction, % of saponified pitch | 33.5 | 35.6 | 50.1 | — | 27.1 |
| | sterol content, % in the fraction | 27.5 | 22.2 | 22.8 | — | 39.7 |
| | sterol content, g * | 40.0 | 437.1 | 29.7 | — | 48.1 |
| | sterol recovery, % of saponified pitch * | 11.1 | 10.0 | 11.4 | — | 12.1 |
| G | first residue, g * | 288.4 | 3562.0 | 129.6 | — | 328.1 |
| | first residue, % of saponified pitch | 66.5 | 64.4 | 49.9 | — | 72.9 |
| Distillation of acid fraction from acidul. first residue | | | | | | |
| H | end pH of acidulation | 2 | 3 | 1.2 | — | 2.5 |
| I | distillation temp. ° C. | 200 | 200 | 230-250 | — | 200 |
| K | pressure, Pa | 200 | 100 | 200 | — | 200 |
| | acid fraction, g * | 63.5 | 1033.0 | 49.2 | — | 183.7 |
| L | acid fraction, % of acidulated first residue | 22 | 29 | 38 | — | 56 |
| M | heavy components, g * | 225.0 | 2529.0 | 80.3 | — | 144.3 |
| | heavy components without softener (calculated) | 151.0 | 1359.3 | 80.3 | — | 91.3 |
| | heavy components, % of acidulated first residue | 78 | 71 | 62 | — | 44 |
| XXX | heavy components incl softener, % of saponified pitch | 62.5 | 58.0 | 30.9 | — | 36.4 |
| | heavy components, % of saponified pitch (without added softener) | 42.0 | 31.2 | 30.9 | — | 23.0 |

TABLE 1-continued

|   |   | EXPERIMENT No (Example) | | | | |
|---|---|---|---|---|---|---|
|   |   | 1 | 2 | 3 | 4 | 5 |
| N | fatty acids, % of acid fraction | 78.3 | 56.6 | 35.4 | — | — |
|   | FA recovery, % of original pitch | 13.8 | 13.4 | 6.7 | — | — |
|   | Composition of acid fraction: | | | | | |
| O | C16 | 3.7 | 3.6 | 4.9 | no analysis | no analysis |
| P | C18 | 1.7 | 1.8 | 2 | | |
| Q | C18:1 | 27.3 | 29.1 | 34.9 | | |
| R | C18:2 | 45 | 42.2 | 38.2 | | |
| S | C18:3 | 1.6 | 1.8 | 2.4 | | |
| T | C18:2 Conj. | 3.1 | 0 | 0 | | |
| U | C20:0 | 2.3 | 2.7 | 2.4 | | |
| V | C20:1 | 6.7 | 7.5 | 6.2 | | |
| X | C20:2 | 1.2 | 1.5 | 1.2 | | |
| Y | C22:0 | 3.9 | 5 | 3.5 | | |
| Z | C22:1 | 0.2 | 0.5 | 0.4 | | |
| Å | C22:2 | 0 | 0.3 | 0.2 | | |
| A | C24:0 | 2.2 | 2.9 | 1.8 | | |
|   | acid value of acid fraction (mg KOH/g) | 175 | 92 | 67 | — | 170 |

\* Due to experimental reasons, the percentage distributions are real figures from distillations, the mass volume calculated from these percentages Explanations:
PP = softener made by evaporation of all the evaporable material from saponified acidulated pitch
P = tall oil pitch
No = no added softener
XXX = "internal softener"

The invention claimed is:

1. A process for recovering sterols and fatty and/or resin acids from tall oil pitch, comprising the steps of:
    a) saponifying tall oil pitch to provide saponified tall oil pitch,
    b) drying the saponified pitch to obtain dried saponified pitch,
    c) subjecting the dried saponified pitch to a first high vacuum evaporation to obtain an unsaponifiable fraction as a distillate and a first residue,
    d) optionally subjecting said distillate to a second high vacuum evaporation to obtain an enriched unsaponifiable fraction,
    e) crystallizing sterols from the unsaponifiable fraction or the enriched un-saponifiable fraction,
    f) acidulating the first residue obtained in step c) to obtain an aqueous phase and an organic phase, separating the aqueous phase and drying the organic phase to obtain a dried organic phase, and
    g) subjecting the dried organic phase to vacuum distillation to obtain fatty and/or resin acids and a second residue,
said process additionally comprising providing a softener having pitch-based heavy components in the dried saponified pitch in an amount sufficient to enable evaporation of the unsaponifiable fraction during the first high vacuum evaporation,
wherein the softener is obtained only from the tall oil pitch.

2. The process of claim 1, wherein the step of providing the softener having pitch-based heavy components comprises recirculating the whole or part of the distillation residue obtained in step g) to the saponified pitch and/or to the dried saponified pitch.

3. The process of claim 1, wherein the step of providing the softener having pitch-based heavy components comprises adding a heavy fraction separated from pitch to the saponified pitch and/or to the dried saponified pitch.

4. The process of claim 1, wherein the step of providing the softener having pitch-based heavy components comprises adding pitch to the saponified pitch and/or to the dried saponified pitch.

5. The process of claim 2, wherein the amount of added said distillation residue, said pitch or said heavy fraction is between 1% and 50% by weight based on the weight of the dried saponified pitch.

6. The process of claim 1, wherein the step of providing the softener having pitch-based heavy components comprises choosing a tall oil pitch naturally having a high content of said heavy components.

7. The process of claim 1, wherein the step of providing the softener having pitch-based heavy components comprises adjusting the degree of the saponification of the pitch.

8. The process of claim 1, wherein the tall oil pitch is saponified by using a stoichiometric excess of sodium or potassium hydroxide or a mixture thereof.

9. The process according to claim 1, wherein the drying in step b) is carried out in a thin film evaporator.

10. The process according to claim 9, wherein the thin film evaporator operates at a temperature in the range of 100° C. to 250° C. and at a pressure in the range of 500 Pa to atmospheric pressure.

11. The process of claim 1, wherein the first high vacuum evaporation of step c) is carried out in a short path evaporator.

12. The process of claim 11, wherein the short path evaporator operates at a temperature in the range of 250° C. to 320° C. and at a pressure of at most 500 Pa.

13. The process of claim 1, wherein the second high vacuum evaporation of step d) is carried out in a thin film evaporator.

14. The process of claim 13, wherein the thin film evaporator includes a fractionation column.

15. The process of claim 13, wherein the thin film evaporator operates at a temperature in the range of 170° C. to 290° C. and at a pressure in the range of 10 to 500 Pa.

16. The process of claim 1, wherein the crystallization step comprises using a solvent or a mixture of solvents comprising at least one or two of the solvents selected from the group consisting of ketones, alkanols, hydrocarbons and water for crystallizing the sterols.

17. The process of claim 1, wherein the vacuum distillation of step g) is carried out at a temperature in the range of 170° C. to 290° C. and at a pressure in the range of 50 to 3000 Pa.

* * * * *